United States Patent
Cho et al.

(10) Patent No.: US 9,035,018 B2
(45) Date of Patent: May 19, 2015

(54) FURAN-BASED CURABLE COMPOUND DERIVED FROM BIOMASS, SOLVENT-FREE CURABLE COMPOSITION, AND METHOD FOR PREPARING SAME

(75) Inventors: Jin Ku Cho, Yongin-si (KR); Sang Yong Kim, Cheonan-si (KR); Do Hoon Lee, Seoul (KR); Bo Ra Kim, Daejeon (KR); Baek Jin Kim, Cheonan-si (KR); Jae Won Jung, Seoul (KR); Sang Hyeup Lee, Daegu (KR); Jae Soung Lee, Seoul (KR)

(73) Assignee: Korea Institute of Industrial Technology, Chungcheongnam-do (KR)

( * ) Notice: Subject to any disclaimer, the term of this patent is extended or adjusted under 35 U.S.C. 154(b) by 425 days.

(21) Appl. No.: 13/394,910

(22) PCT Filed: May 11, 2010

(86) PCT No.: PCT/KR2010/002971
§ 371 (c)(1),
(2), (4) Date: May 18, 2012

(87) PCT Pub. No.: WO2011/030991
PCT Pub. Date: Mar. 17, 2011

(65) Prior Publication Data
US 2012/0220742 A1    Aug. 30, 2012

(30) Foreign Application Priority Data
Sep. 8, 2009 (KR) .................. 10-2009-0084416

(51) Int. Cl.
*C08G 59/02* (2006.01)
*C07D 407/14* (2006.01)
(Continued)

(52) U.S. Cl.
CPC ............... *C07D 407/14* (2013.01); *C08F 2/48* (2013.01)

(58) Field of Classification Search
CPC ................................................ C07D 405/14
USPC ................................................ 528/403, 425
See application file for complete search history.

(56) References Cited

U.S. PATENT DOCUMENTS 5,512,613 A   4/1996   Afzali-Ardakani et al.
6,825,315 B2  11/2004  Aubert

FOREIGN PATENT DOCUMENTS

EP   0283951 A1    9/1988
JP   2006193629 A  7/2006

OTHER PUBLICATIONS

Sorokin et al; Synthesis of epoxy-furan resins; 1967; Russian journal; Chem Abstract 70:78664.*

(Continued)

*Primary Examiner* — Duc Truong
(74) *Attorney, Agent, or Firm* — Dority & Manning, P.A.

(57) ABSTRACT

The present invention relates to a furan-based curable compound derived from carbohydrate-based biomass, to a solvent-free curable composition, and to a method for preparing thereof, wherein the furan-based curable compound derived from biomass according to the present invention includes two epoxide functional groups bonded to at least one furan-based compound. The present invention may provide an environmentally friendly next-generation curable compound comprising a novel furan-based compound derived from biomass, which may be substituted for curable materials derived from oil resources, as a basic backbone, as well as a composition containing the same. According to the present invention, a curable material, which has a low contraction ratio during curing as compared to conventional radical-type curing materials, may be obtained, and a compound applied to the novel curing material may be prepared with a combination of excellent efficiency and cost-effectiveness.

3 Claims, 4 Drawing Sheets

(51) Int. Cl.
*C08F 2/48* (2006.01)
*C08G 65/00* (2006.01)

(56) References Cited

OTHER PUBLICATIONS

Abstract of Article—"Removable Foams Based on an Epoxy Resin Incorporating Reversible Diels-Alder Adducts," McElhanon et al., Journal of applied Polymer Science, vol. 85, Issue 7, Aug. 15, 2002, pp. 1496-1502, 2 pages.
Abstract of Article—"Special-Purpose Epoxy Adhesives," Kochergin et al., Polymer Science Series C, vol. 49, No. 1, 2006, pp. 17-21, 1 pages.
Search Report for PCT/KR2010/002971 dated Jan. 26, 2011, 2 pages.

* cited by examiner

FURAN-BASED CURABLE COMPOUND DERIVED FROM BIOMASS, SOLVENT-FREE CURABLE COMPOSITION, AND METHOD FOR PREPARING SAME

CROSS REFERENCE TO RELATED APPLICATION

This application is the national stage entry of International Patent Application No. PCT/KR2010/002971 having a filing date of May 11, 2010, which claims priority to and the benefit of Korean Patent Application No. 10-2009-0084416 filed in the Korean Intellectual Property Office on Sep. 8, 2009, the entire contents of which are incorporated herein by reference.

TECHNICAL FIELD

The present invention relates to a furan-based curable compound derived from biomass, a solvent-free curable composition, and a method for preparing thereof. More specifically, it is suggested to replace materials derived from oil resources used as sources for adhesives or tacky agent, sealant, coating agents and the like with the present invention. The present invention provides a curable compound prepared using a furan-based compound derived from biomass instead of petrochemical-derived materials, a solvent-free curable composition and a method for preparing the same.

BACKGROUND ART

Adhesive materials including adhesives, tacky agent, sealant, coating agents, paints and the like are utilized in the industries ranging from civil engineering, architecture to packaging, bookbinding, automobile, electronics, fine chemicals, optics, carpentry, plywood, fabrics, leather as well as for domestic purposes, and their use has indeed become largely extensive. Applications of the adhesive materials include a variety of wood, metal, rubber, plastic, leather, ceramics and so forth, and recently concrete has been added to the above list.

These adhesives which are prepared in the form of a mixture of chemical substances which mainly uses synthetic resins generate toxic substances such as VOC (volatile organic compound), dioxin and endocrine disrupting chemicals due to an organic solvent used in preparing and the diverse volatile additives being added to improve properties. Recently the production and use of these toxic substances are strictly restricted by the international agreement on the environmental regulations. Furthermore, these regulations are used as a novel means of trade sanctions by EU and the like. To keep pace with the current, conventional solvent adhesives are gradually being replaced by those that are water-soluble, solvent-free and hot-melt.

Moreover, while most of the fine chemical materials as well as these adhesive materials are petrochemicals derived from oil refinery process, the global oil price is steadily increasing due to the decrease in its reserves and the surge in demand especially driven by BRICs. As the international agreement strictly regulating greenhouse gas emissions takes effect, it is expected that using irreversible fossil resources such as oil would take great toll on the environment.

Therefore, there are many efforts being made so as to obtain fine chemical products, from instead of oil resources, yet from novel resources onwards, the most typical source to use being carbohydrate-based biomass. [Ghheda, J. N.; Huber, G. W.; Dumesic, J. A. Angew. Chem. Int. Ed. 2007, 46, 7164-7183, Corina, A.; bona, S.; Velty, A. Chem. Rev. 2007, 107, 2411-2502.] A considerable amount of about 170 billion tons of carbohydrate are produced in nature through photosynthesis every year. Humankind however makes merely about 3% use of the total carbohydrate produced for food, paper, furniture, construction materials and so forth.

Consequently, the fine chemicals prepared from renewable and sustainable carbohydrate-based biomass are anticipated to be able to offer alternatives to the petrochemicals. More specifically, how to synthesize a compound containing some sort of adhesiveness or tackiness by using the carbohydrate-based biomass need be further studied in order to replace curable adhesive materials derived from conventional oil resources.

On the other hand, curable, particularly, photo-curable adhesive materials containing an acrylate-based or isocyanate-based functional group generally carry a rapid-curing property at a room temperature through a radical polymerization, wherein, however, lies a problem of causing large contraction due to the rapid curing rate. Due to the excessive contraction, the demand for introducing the materials with low contraction ratio after curing is currently present in the field where adhesive materials are used and especially in those of electronic materials and such where precise dimensional stability is required.

DETAILED DESCRIPTION OF THE INVENTION

Technical Problem

This invention hence aims to solve those problems, wherein the purpose is to provide a furan-based curable compound derived from carbohydrate-based biomass as a basic backbone, which may replace an aromatic compound produced through a petrochemical process. In addition, the present invention may also provide a novel curable compound, which may reduce curing contraction ratio, and a method for preparing thereof with a combination of high yield and cost-effectiveness.

Another purpose of the present invention serves to use as adhesive materials an environmentally friendly solvent-free curable composition comprising such a curable compound.

Solution to Problem

This invention intends to solve those problems, wherein a furan-based curable compound derived from biomass according to an embodiment of the present invention comprises two epoxide functional groups bonded to at least one furan-based compound.

More specifically, the furan-based curable compound derived from biomass is having the following chemical structure I or chemical structure II.

[Chemical structure I]

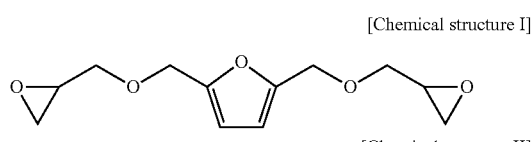

[Chemical structure II]

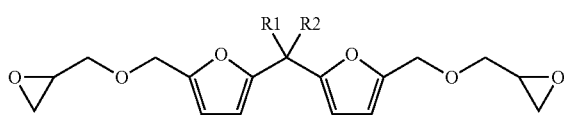

In the chemical structure II, $R_1$ or $R_2$ may be one of hydrogen, alkyl group, alkenyl, alkynyl, cycloalkyl or aryl group.

Furthermore, a solvent-free curable composition according to an embodiment of the invention comprises the furan-based curable compound derived from biomass and an initiator.

It is desirable that the initiator herein be a cationic curing initiator.

A method for preparing a furan-based curable compound derived from biomass according to an embodiment of the invention comprises a step of preparing a starting material wherein a furan-based compound derived from biomass is prepared as a starting material which may be obtained through oxidation or reduction reaction by using as an intermediate furfural or furfural derivatives converted from a cellulose or hemicellulose extracted from carbohydrate-based biomass; and a step of mixing and stirring the furan-based compound derived from biomass and an epichlorohydrin.

The furan-based compound derived from biomass herein is preferably 2,5-furandimethanol or the compound having the following chemical structure III.

[Chemical structure III]

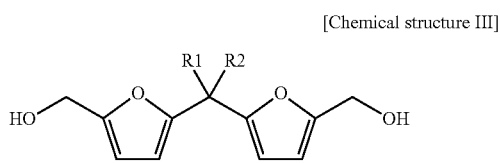

In the chemical structure III, $R_1$ or $R_2$ may be one of hydrogen, alkyl group, alkenyl, alkynyl, cycloalkyl or aryl group.

In addition, in the step of mixing and stirring, it is desirable to ensure that the mixture comprising the furan-based compound derived from biomass and the epichlorohydrin is reacted using PTC (Phase Transfer Catalyst) as a catalyst in a bi-phasic solvent system where a sodium hydroxide aqueous solution is added.

Furthermore, it is desirable to set the equivalent weight of the epichlorohydrin at 5 to 20. According to an embodiment of the invention, a method for preparing a solvent-free composition comprises a step of preparing a composition wherein a curable adhesive composition is prepared by mixing the furan-based curable compound derived from biomass prepared by the method for preparing the furan-based curable compound derived from biomass, and cationic curing initiator or curing agent.

Advantageous Effects of the Invention

The present invention may provide an environmentally friendly next-generation curable compound comprising a novel furan-based compound derived from biomass as a basic backbone as well as a composition containing thereof, which may replace curable materials derived from oil resources.

According to the present invention, a curing material which has a low contraction ratio during curing as compared to that of a conventional radical-type curing material, may be obtained, and a compound applied to such a novel curing material may be prepared with a combination of excellent efficiency and cost-effectiveness.

BEST MODE FOR CARRYING OUT THE INVENTION

Figure 1:
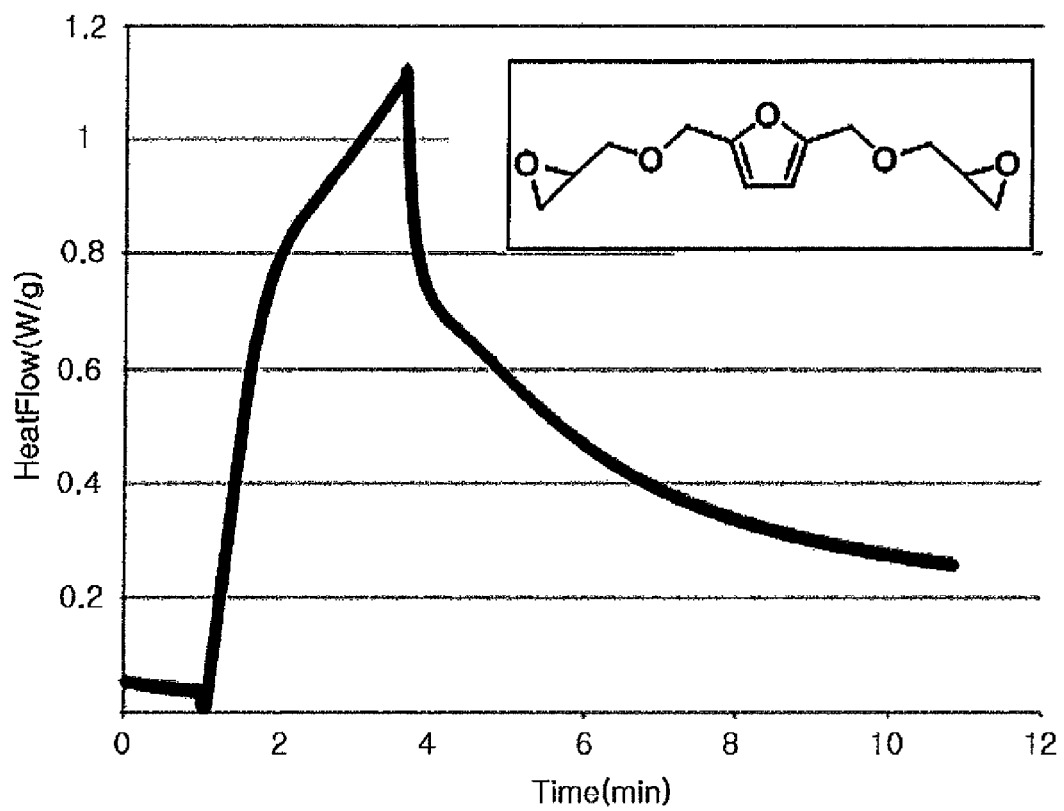
FIG. 1 refers to the result of measuring a photo-curable behavior by Photo-DSC of a curable compound prepared according to preparation example 1 of the invention.

The present invention delves into solutions to those problems, wherein a furan-based curable compound derived from biomass according to the invention has an oligomer monomeric structure, and comprises two epoxide functional groups bonded to at least one furan-based compound.

In other words, this invention intends to replace an aromatic compound produced through a petrochemical process by applying as a basic backbone the furan-based compound derived from carbohydrate-based biomass.

Carbohydrate-based biomass as shown in the following chemical reaction formula typically contains about 30 to 40% of cellulose and about 10 to 20% of hemicellulose, both of which are extracted to carry out saccharification through hydrolysis or enzymatical treatment under an acid catalyst to obtain a hexose or pentose compound. The hexose or pentose compound may obtain a furfural intermediate compound such as 5-hydroxymethyl-2-furfural (HMF) or 2-furfural again by catalysis, and successively through reduction or oxidation may also obtain a furan-based compound which has an alcohol functional group such as 2,5-furan dimethanol or has a carboxylic acid functional group such as 2-furan carboxylic acid.

[Chemical reaction formula I]

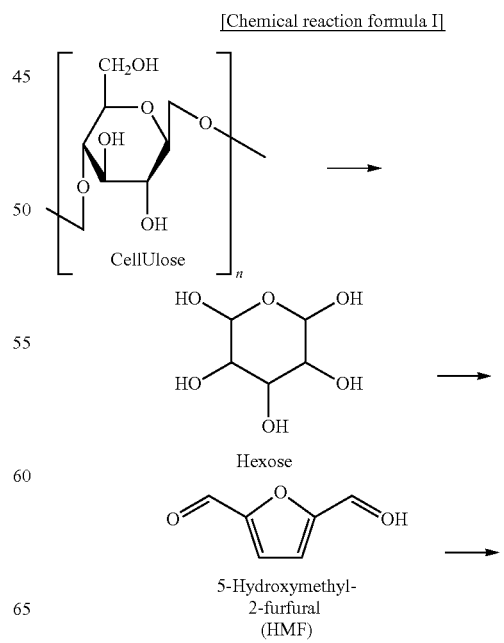

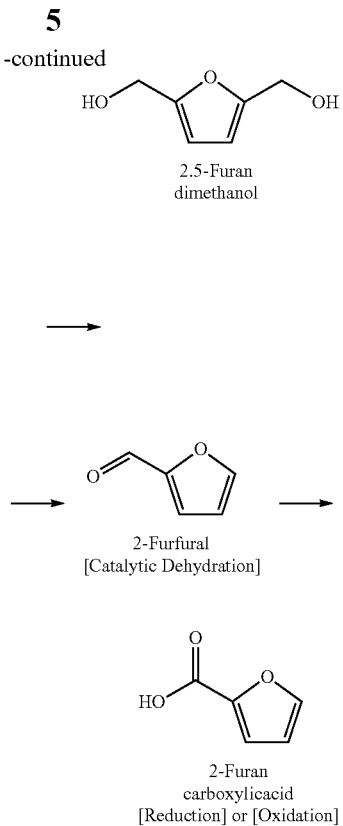

ion, and by reducing (for example, hydrogenation) the α-azide alcohol formed. The reaction of other nucleophiles produces a functionalized compound which may be converted to likewise useful materials. If added with Lewis acid, it may operate as an epoxide activator. The epoxide is not known until now about the likelihood of being applied as a curing material in which the epoxide functional group is introduced into the furan-based compound derived from renewable resources although there are examples of the epoxide used for the adhesives, tacky agents, sealant and coating agents as a functional group of curing material.

Therefore, according to the present invention, by introducing the epoxide into the furan-based compound derived from renewable resources as the functional group of curing material and thereby replacing chemical products derived from petrochemicals, it may be possible to overcome the setbacks caused by depletion of oil resources as well as to obtain the curing material with significantly reduced contraction ratio. In addition, the furan-based compound derived from biomass according to the invention may be formed by linking one or more epoxide functional groups to a furan central ring.

Detailed embodiments of the furan-based compound derived from biomass according to the invention are represented in chemical structure I or chemical structure II below.

The furan-based compound prepared as in the above reaction is known to be available as an alternative compound to an aromatic substance since it has similar chemical and physical properties to those of an aromatic compound prepared through a petrochemical process [Gandini, A.; Belgaern, M. N. *Prog. Polym. Sci.* 1997, 22, 1203-1379]. The furan-based compound used in the invention is not particularly restricted if capable of forming a furan ring at the center of the curable compound prepared. In addition, this furan ring may be formed by linking one or more rings. This is to be further described in a preparing method hereinafter.

On the other hand, an epoxide bonded to the furan-based compound serving as a basic backbone is applied in the invention to increase the degree-of-freedom in molecular structure due to ring-opening reaction of a cyclic molecule, and consequently, to decrease in curing contraction ratio. The ring-opening reaction of the functional group is induced in a compound (oligomer monomer) by introducing this epoxide group, such that it prevents drastic contraction of a curing material, thus obtaining a curable compound with significantly reduced curing contraction ratio and a curable composition comprising the compound for adhesive. Since the curing material comprising the epoxide functional group is proceeded according to ion mechanism during curing, its feature is that it takes longer to cure compared to acrylic, vinyl-based and styrene-based materials, which follow radical curing mechanism, and advantageously has low curing contraction ratio due to the effect of expansion of the molecular structure since the curing is conducted by the ring opening reaction as the epoxide ring structure opens.

The epoxide is an intermediate useful in three-dimensionally regulated synthesis of a complex organic compound due to the diversity of compounds which may be produced by the ring opening reaction. For example, α-amino alcohol may be obtained simply by ring-opening the epoxide to form an azide

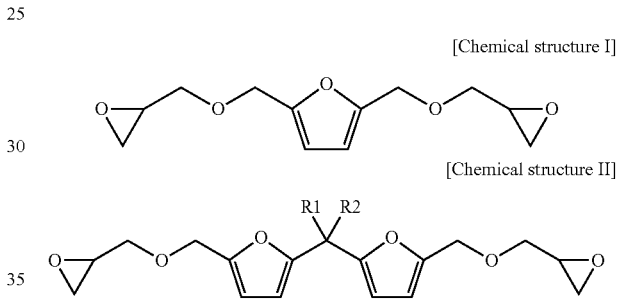

[Chemical structure I]

[Chemical structure II]

In the chemical structure II, $R_1$ or $R_2$ may be one of hydrogen, alkyl group, alkenyl, alkynyl, cycloalkyl or aryl group.

It is desirable herein that 2,5-furan dimethanol, of which the synthesis method is described above, be used as a starting material of the compound having the chemical structure I, and the compound having the chemical structure III be used as a starting material of the compound having the chemical structure II. The compound having the chemical structure III may be prepared by reduction reaction of the compound having chemical structure IV which is obtained from 2-furan carboxylic acid, of which the synthesis method is described earlier.

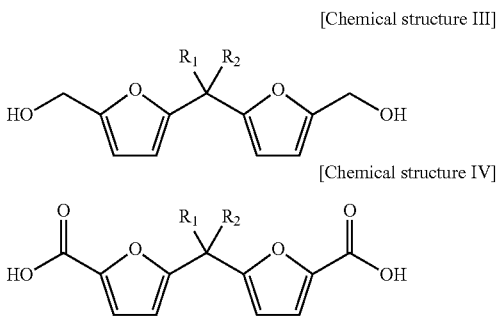

[Chemical structure III]

[Chemical structure IV]

In the chemical structure III and the chemical structure IV, $R_1$ or $R_2$ may be one of hydrogen, alkyl group, alkenyl, alkynyl, cycloalkyl or aryl group.

The method for preparing the furan-based curable compound derived from biomass according to the invention is to be described hereinafter.

Above all, the method for preparing the furan-based compound introduced with the two epoxide functional groups using 2,5-furan dimethanol obtainable from a cellulose extracted from carbohydrate-based biomass as a starting material, is applied firstly by ① reacting a hydroxy group of the starting material with NaH (sodium hydride) under anhydrous organic solvent to convert to alkoxide and then substituting epichlorohydrin, and then by ② reacting with an anhydrous carbonate metallic salt such as $K_2CO_3$ or $Cs_2CO_3$ under polar organic solvent such as N,N-dimethylformamide (DMF), however, it wasn't successful in efficiently synthesizing the target compound. Accordingly, as a new method, the method for preparing the furan-based curable compound derived from biomass according to the invention has been suggested. As a result of conducting the method for preparing the furan-based curable compound according to the invention, the target compound could be synthesized with excellent yield.

The method for preparing the furan-based curable compound derived from carbohydrate-based biomass according to the invention comprises a step of preparing a starting material S10 wherein a furan-based compound is prepared as a starting material using a cellulose extracted from carbohydrate-based biomass; and a step of mixing and stirring S20 the furan-based compound derived from biomass and an epichlorohydrin.

The step of preparing a starting material S10 wherein a furan-based compound is prepared as a starting material is not particularly restricted if only the method can prepare the furan-based compound which is already known, so that an optional method may be used for preparing any type of furan-based compound.

For example, as an embodiment of the step of preparing a starting material S10 wherein a furan-based compound is prepared as a starting material, a method for preparing 2,5-furan dimethanol as a starting material is as shown in the chemical reaction formula 1 described above. Furthermore, in the chemical reaction formula 1, hexose material having a six-membered ring system (pyranose)—for example, glucose, galactose, and so on-produced through hydrolysis of a cellulose is used to produce an intermediate, HMF. However, as indicated in the following chemical reaction formula 2, if hexose material having a five-membered ring system (furanose) such as fructose is used, since the intermediate, HMF has the same five-membered ring system, it is relatively easy to obtain HMF. In addition, in preparing the intermediate, HMF, conventional inorganic acid catalysts such as sulfuric acid or hydrochloric acid, or Lewis acid catalyst with various ligands coordinated in metal for the purpose of increasing activation and selectivity may be used. However, a heterogeneous solid acid catalyst or a heterogeneous metal catalyst may also be used which may solve the problems of isolation and purification occurring while using those homogeneous catalysts and facilitate reusing and using in a continuous process.

[Chemical reaction formula 2]

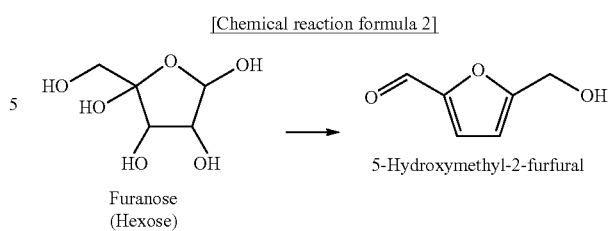

Furanose
(Hexose)

5-Hydroxymethyl-2-furfural

The method for preparing 2,5-furan dimethanol as a starting material is as shown in the chemical reaction formula 1 illustrated above.

On the other hand, a method for preparing the compound having the chemical structure III as a starting material comprises, as represented in the following chemical reaction formula 3, refluxing 2-furan carboxylic acid in methanol solvent in the presence of hydrochloric acid (HCl) to be converted to 2-furan carboxylic acid methyl ester. The 2-furan carboxylic acid methyl ester formed is reacted with aldehyde or ketone in sulfuric acid to synthesize a compound having the chemical structure IV and then is to be reduced to alcohol. As a result, the compound having the chemical structure III is synthesized. The compound having the chemical structure III is a furan-structured compound, which has a similar structure with an epoxy-based compound, bisphenol A used as a primary intermediate in synthesizing polymer in general, and is expected to show a similar behavior and properties with the bisphenol A.

[Chemical reaction formula 3]

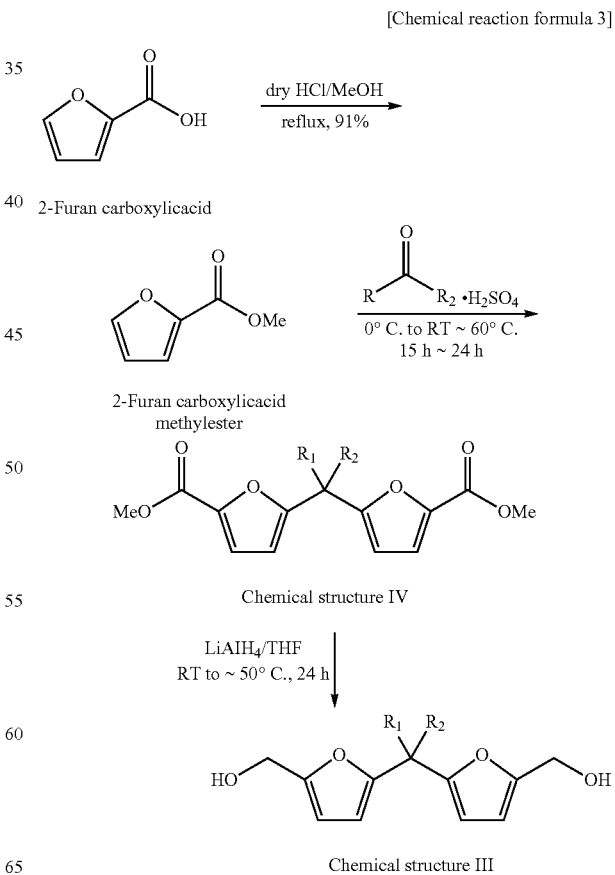

The step of mixing and stirring S20 is a step wherein 2,5-furandimethanol prepared through the step of preparing a starting material S10 wherein a furan-based compound is prepared as a starting material or the furan-based compound having the chemical structure III is used as a starting material, into which an epichlorohydrin is added as a material to introduce an epoxide functional group, and then reacted by stirring with the furan-based compound.

As a detailed embodiment of the step of mixing and stirring S20, it is desirable that a mixture containing the furan-based compound and the epichlorohydrin be reacted using PTC (Phase Transfer Catalyst) as a catalyst in a bi-phasic solvent system where a sodium hydroxide (NaOH) aqueous solution is added.

PTC may include tetrabutylammonium bromide (TBABr), tetrabutylammonium chloride, tetraoctylammonium chloride, tetrabutylammonium hydrogen sulfate, methyltrioctylammonium chloride, hexadecyltrimethylammonium chloride, hexadecyltrimethylammonium bromide, benzyltrimethylammonium chloride, benzyltriethylammonium chloride, benzyltrimethylammonium hydroxide, benzylhiethylammonium hydroxide, benzyltributylammonium chloride, benzyltributylammonium bromide, tetrabutylphosphonium bromide, tetrabutylphosphonium chloride, tributylhexadecylphosphonium bromide, butyltriphenyiphosphonium chlroride, ethyltrioctylphosphonium bromide, tetraphenylphosphonium bromide and so forth, and apart from those above, PTC may not be particularly limited.

In addition, it is desirable that the equivalent weight of epichlorohydrin be from 5 to 20, and more preferably, from 10 to 15.

A detailed embodiment of the step of mixing and stirring S20 is as indicated in the following chemical reaction formula 4, That is, tetrabutylammonium bromide (TBABr) is added as PTC in a bi-phasic solvent system of epichlorohydrin and NaOH aqueous solution, while 2,5-furandymethanol as a starting material is dissolved in a tetrahydrofuran (THF) solvent separately, which is then reacted by slowly being added by drops in the bi-phasic solvent system to obtain the target material, 2-functional groups epoxy monomer having the chemical structure I.

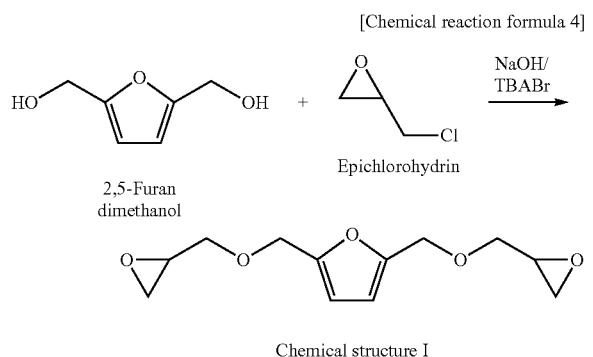

[Chemical reaction formula 4]

Chemical structure I

Another embodiment of the step of mixing and stirring S20 is to use the compound having the chemical structure III as a starting material, and its reaction mechanism is as indicated in the following chemical reaction formula 5. Therefore, such that 2,5-furandymethanol is used as a starting material, the compound having the chemical structure II, which is an epoxy monomer comprising the two functional groups and two furan rings, may be synthesized by reacting the epichlorohydrin and the compound having the chemical structure III in the bi-phasic solvent system in the presence of PTC.

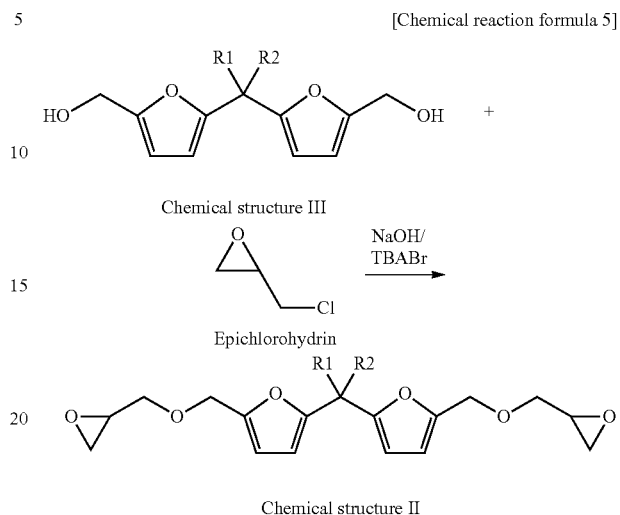

[Chemical reaction formula 5]

Chemical structure III

Epichlorohydrin

Chemical structure II

Furthermore, a solvent-free curable composition may be obtained by comprising and conducting the step of preparing a composition wherein a curable adhesive composition is prepared by adding and mixing the furan-based curable compound derived from biomass prepared according to the above-stated method for preparing the compound, and other curable oligomer compounds, initiators such as photo initiator or thermal initiator or other additives. Preferably, the photo initiator or curing agent used in a typical epoxy resin composition is used in order to conduct UV curing as well as photo curing.

In case of conducting photo-initiation, since the furan-based curable compound derived from biomass according to the invention is a cationic curable (or polymerizable) compound which is polymerized through cationic polymerization and cured, it is desirable to use a cationic curing initiator (polymerization initiator) as a curing initiator. As for the cationic curing initiator, those that are able to cationically polymerize the furan-based curable compound derived from biomass with relatively low energy, by generating a cationic polymerization initiator which is activated by light irradiation, are available for use without restriction. An ionic photoacid-generating photocationic polymerization initiator or nonionic photoacid-generating photocationic polymerization initiator may either be used for the cationic curing initiator. Furthermore, the added quantity of the cationic curing initiator is not particularly limited, which preferably is to be set up appropriately dependent on reactivity or molecular weight of the compound derived from biomass, or degree of viscoelasticity which is to be given to the curable composition prepared using the compound derived from biomass. However, if the added quantity of the cationic curing initiator is too much, curing by light irradiation occurs exceedingly fast since the reactivity of the curable composition grows sharply, which could cause trouble in the following steps. On the other hand, if too little, curing of the curable composition may not be proceeded enough or delay in the curing rate may occur. Therefore, about 0.1 to 15 w %, preferably, 0.2 to 12.5 w % of the added quantity of the cationic curing initiator for the entire curable composition may be added.

The ionic photoacid-generating photocationic polymerization initiator, for example, includes aryldiazonium salts, diarylhalonium salts, aromatic sulfonium salts such as triarylsulfonium salts or onium salts such as triphenylphosphonium salts; and organometallic complexes such as iron-arene complex, titanocene complex or arylsilanol-aluminium complex. In addition, the nonionic photoacid-generating photocationic polymerization initiator, for example, includes nitrobenzyl ester, sulfonic acid derivatives, photphate ester, phenolsulfonic acid ester, diazonaphthoquinone or N-hydroxyimidesulfonate, and those may be used alone or combined.

Furthermore, more than one free radical polymerizable compound having more than one ethylenically unsaturated group such as acrylate (i.e. acrylate and/or methacrylate) functional group may be contained in the composition above in order to compensate rather slow curing rate of the compound according to the present invention. In case of containing the free radical polymerizable compound in a composition, more than one free radical photo initiator may be used as a photo initiator along with the cationic curing initiator.

Examples of such a free radical photo initiator include benzophenone (for example, benzophenone, alkyl-substituted benzophenon or alkoxy-substituted benzophenone); benzoin, for example, benzoin, benzoin ether (for example, bezonin methylether, benzoin ethyl ether and benzoin isopropyl ether), benzoin phenyl ether and benzoin acetate; acetophenone such as acetophenone, 2,2-dimethoxyacetophenone, 4-(phenyltio)acetophenone and 1,1-dichloroacetophenone, benzyl, benzyl ketal (for example, benzyl dimethyl ketal and benzyl diethyl ketal); anthraquinone such as 2-methylanthraquinone, 2-ethylanthraquinone, 2-tert-butylanthraquinone, 1-chloroanthraquinone and 2-amylanthraquinone; triphenylphosphine; for example, benzoylphosphine oxide such as 2,4,6-trimethylbenzoyldiphenylphosphine oxide; thioxantone and xantone, acridin derivatives, phenazine derivatives, quinoxaline derivatives or 1-phenyl-1,2-propanedion-2-0-benzoyloxime, 1-aminophenyl ketone or 1-hydroxyphenyl ketone (for example, 1-hydroxicyclohexyl phenyl ketone, phenyl(1-hydroxyisopropyl)ketone and 4-isopropylphenyl(1-hydroxyisopropyl)ketone), or triazine compound, for example, 4-methyl thiophenyl-1-di(trichloromethyl)-3,5-S-triazine,S-triazine-2-(stilbene)-4,6-bis-trichloromethyl and parametoxy styryl triazine and so forth, and those may be used alone or combined.

On the other hand, in preparing a solvent-free curable composition according to the invention, a curing agent contained in a typical epoxy resin composition may be used instead of the photo-curable agent. In such a case where the curing agent is used, curing may be conducted in a general manner of using epoxy resin instead of photo curing. Types of the curing agent include amine, acid anhydride, amide, or phenol compound. Detailed examples of the curing agent are not limited to but include diaminodiphenylmethane, diethylenetriamine, triethylenetetramine, diaminodiphenylsulfon, isophorondiamine, dicyandiamide, polyamide resin synthesized from linolenic acid dimer and ethylenediamine, phthalic anhydride, trimellitic anhydride, pyromellitic anhydride, maleic anhydride, tetrahydrophthalic anhydride, methyltetrahydrophthalic anhydride, methylnadic anhydride, hexahydrophthalic anhydride, methylhexahydrophthalic anhydride, phenol novolak and its modifications, imidazole, BF3-amine complex and quinidine derivatives. Such curing agents may be used alone or combined by two or more. In addition, the quantity of the curing agent which may be used for the curable composition of the invention is desirable to be added in accordance with the quantity of the photo initiator stated above.

Aside from those above, the solvent-free curable composition according to the present invention may use a mixture of various additives such as a curing accelerator, an inorganic filler, a release agent and pigment, etc.

For example, the curing accelerator may be used along with the curing agent, and detailed examples of the curing accelerator which may be used in the present invention include imidazole such as 2-methylimidazole, 2-ethylimidazole and 2-ethyl-4methyl-imidazole; 2-(dimethylaminomethyl)phenol and tertiary amine such as 1,8-diaza-bicyclo (5.4.0)-undecane-7; phosphine such as triphenylphosphine; and metallic compound such as octylic stannum. Based on 100 parts of the furan-based curable compound derived from biomass according to the invention is added from 0.01 to 10 parts by weight of the curing accelerator, preferably from 0.2 to 5 parts by weight of the curing accelerator.

The inorganic filler may also be mixed depending on the type of the solvent-free curable composition according to the present invention. Specific examples of the available inorganic filler include silica, alumina and talc. The solvent-free curable composition according to the invention may also contain release agents such as a silane coupling agent, a stearic acid, a palmitic acid, a zinc stearate and a calcium stearate and pigments as well as various mixing additives.

Preferably, the preparing a composition may be conducted by fully mixing and homogenizing the components of the composition produced as such, for instance, by means of an extruder, a kneader, or a roll, etc.

MODE FOR THE INVENTION

The furan-based curable compound derived from biomass according to the invention is to be described with reference to the following preparation examples, experimental example and comparative example.

Preparation Example 1

Preparing the Compound Having Chemical Structure I 22 ml of epichlorohydrin and tetrabutylammonium bromide (TBABr) as PTC in a bi-phasic solvent system of NaOH aqueous solution (19.2 g, 240 mmol) of 50% are put into a 100 mL round-bottom flask one after another, which then are intensely magnetic stirred. Afterwards a diluted starting material, 2,5-furandimethanol (2.56 g, 19.9 mmol) is slowly added by drops into about 30 mL of tetrahydrofuran (THF) at a room temperature later to be intensely stirred at 50° C. for 2 hours. The reaction liquid is then moved to a separatory funnel, into which are added distilled water and ethylacetate (EtOAc) 200 ml each to wash an organic layer twice and washed with saturated NaCl aqueous solution. After moisture in the funnel is removed by $MgSO_4$, the residue having been filtered and vacuum evaporated is separated by flash chromatography (hexanes:EtOAc=7:4) to obtain a furan-based compound containing two epoxide functional groups (2.564 g, 10.6 mmol, 54% of yield) in the form of transparent oil. The data of $^1H$ and $^{13}C$-NMR referring to that is as below.

$^1H$ NMR (400 MHz, $CDCl_3$): δ 6.32-6.28 (m, 1H), 4.58-4.46 (m, 2H), 3.80-3.74 (m, 1H), 3.48-3.40 (m, 1H), 3.20-3.18 (m, 1H), 2.82-2.78 (m, 1H), 2.64-2.58 (m, 1H).

$^{13}C$ NMR (100 MHz, $CDCl_3$): δ 152.0, 110.5, 110.4, 70.9, 65.3, 50.9, 44.4.

Preparation Example 2

Preparing a Compound in which $R_1$ or $R_2$ is Hydrogen in Chemical Structure II, Using as a Starting Material A Compound in which $R_1$ or $R_2$ is Hydrogen in Chemical Structure III (1) Preparing 2-Furan Carboxylic Acid Methyl Ester (The First Intermediate)

[Chemical reaction formula 6]

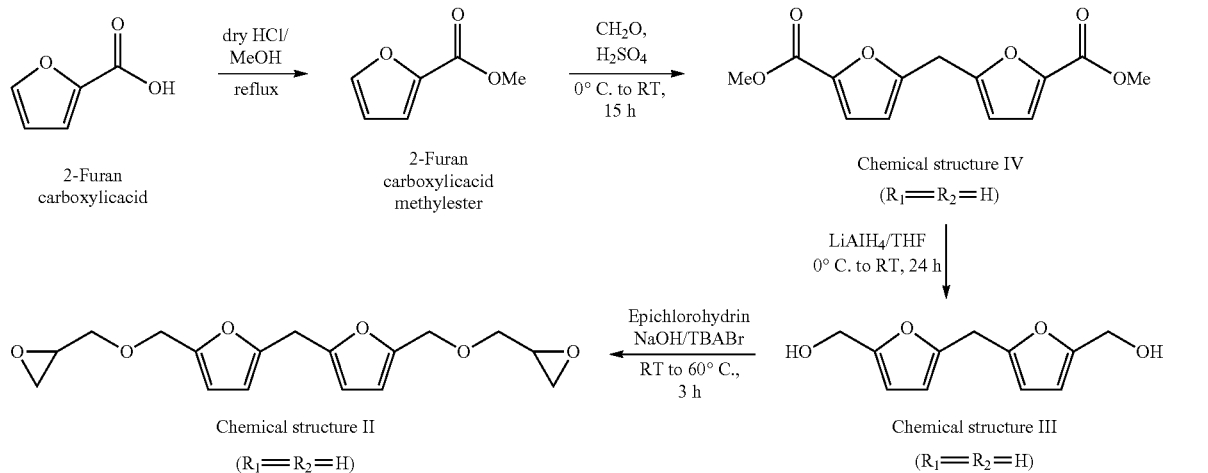

With reference to the chemical reaction formula 6, 2-furan carboxylic acid (20 g, 178 mmol) and 0.5M of HCl/methanol (400 mL) are put in one after another to be dissolved in an 1 L round-bottom flask and are refluxed at 80° C. for 2 hours to be reacted. After the solvent is removed by vacuum drying, the residue from which is diluted in EtOAc to be moved to a separatory funnel, and washed in turn with ice water and 5% of sodium bicarbonate ($NaHCO_3$) aqueous solution, with pH checked at 7~8 at the end. After moisture in the funnel is removed by $MgSO_4$, the residue having been filtered and vacuum evaporated is separated by flash chromatography (hexanes: EtOAc=10:1) to obtain a 2-furan carboxylic acid methyl ester (20.53 g, 162 mmol, 91% of yield), in the form of light yellow oil. The data of $^1H$ and $^{13}C$-NMR referring to that is as below.

$^1H$ NMR (400 MHz, $CDCl_3$): δ 7.60-7.58 (m, 1H), 7.19 (d, J=3.6 Hz, 1H), 6.54-6.50 (m, 1H), 3.90 (s, 3H).

$^{13}C$ NMR (100 MHz, $CDCl_3$): δ 159.4, 146.6, 146.5, 144.7, 118.2, 112.1, 112.0, 52.2, 32.1.

(2) Preparing the Compound (The Second Intermediate) Having Chemical Structure IV ($R_1=R_2=H$)

Afterwards $H_2SO_4$ (15 ml) of 98% is put into a 25 mL round-bottom flask, from which the reaction liquid is then cooled to −5~0° C. in the presence of argon atmosphere by ice-salt bath. With the temperature maintained throughout, after the compound (1.5 g, 12 mmol) synthesized in the previous step is added into the flask, formaldehyde (0.50 mL, 24 mmol) of 35% is slowly added by drops, from which the ice-salt bath is removed and then reacted at a room temperature for an hour. The color of the reaction liquid at this point changes from navy blue to reddish brown. After the reaction liquid is put into a sufficient amount of crushed ice and moved to a separatory funnel using water and EtOAc, an organic layer is washed with distilled water and 5% of $NaHCO_3$ (sodium bicarbonate) in turn. After moisture from the collected organic layers is removed by $MgSO_4$, the residue having been filtered and vacuum evaporated is separated by flash chromatography (hexanes:EtOAc=6:1) and recrystallized (EtOAc-hexane) to obtain a compound (1.358 g, 5.13 mmol, 85% of yield) of chemical structure IV ($R_1=R_2=H$) in the form of light brown crystallization. The data of $^1H$ and $^{13}C$-NMR referring to that is as below.

$^1H$ NMR (400 MHz, $CDCl_3$): δ 7.13 (d, J=3.6 Hz, 2H), 6.27 (d, J=3.6 Hz, 2H), 4.16 (s, 2H), 3.89 (s, 6H)

$^{13}C$ NMR (100 MHz, $CDCl_3$): δ 159.2, 154.8, 144.1, 119.4, 119.4, 110.0, 109.9, 52.2, 52.1, 28.2.

(3) Preparing the Compound Having Chemical Structure II ($R_1=R_2=H$)

$LiAlH_4$ (350 mg, 9 mmol) and anhydrous THF (10 mL) are put into a 50 mL round-bottom flask and then stirred in the presence of argon atmosphere. The dark gray suspension formed is then cooled by ice-bath, into which is slowly added by drops after being diluted in anhydrous THF (10 mL), the compound (1.2 g, 4.54 mmol) synthesized in the previous step. Afterwards the ice-bath is removed from the flask, within which reaction by stirring occurs at a room temperature for 24 hours. Upon the completion of the reaction, saturated sodium sulfate aqueous solution is slowly added by drops while again using the ice-bath to remove $LiAlH_4$ used in excess. It is possible at this point to check that the reaction liquid in the dark gray suspension state changes to a white slurry form. The reaction liquid is then filtered through the filter applying celite and washed with a sufficient amount of $CH_2Cl_2$ and $CH_3CN$-EtOAc (1:9) in turn. After a moisture from all the collected organic filtrates is removed by $MgSO_4$, the residue having been filtered and vacuum evaporated is separated by flash chromatography (hexanes:EtOAc=5:2) and recrystallized (EtOAc-hexanes) to obtain a compound (726 mg, 2.59 mmol, 57% of yield) having chemical structure III ($R_1=R_2=H$) in the form of white crystallization. The data of $^1H$ and $^{13}C$-NMR referring to that is as below.

$^1H$ NMR (400 MHz, $CDCl_3$): δ 6.22 (d, J=2.8 Hz, 2H), 6.05 (d, J=2.8 Hz, 2H), 4.56 (d, J=5.2 Hz, 4H), 3.98 (s, 2H), 1.73 (t, J=5.6 Hz, 2H)

$^{13}C$ NMR (100 MHz, $CDCl_3$): δ 153.3, 151.7, 109.1, 108.9, 107.6, 107.5, 57.7, 27.8.

(4) Preparing the Compound Having Chemical Structure II ($R_1=R_2=H$) (Reacting Step)

Using a compound (500 mg, 2.4 mmol) having chemical structure III ($R_1=R_2=H$), epichlorohydrin (3.7 mL, 47 mmol), 50% of NaOH aqueous solution (3.2 g, 40 mmol) and tetrabutylammonium bromide (100 mg, 0.31 mmol) as PCT, reaction and work-up are conducted under the same synthesizing condition as that of the preparation example 1. The reaction liquid is then separated by flash chromatography (hexanes:EtOAc=6:5) to obtain a compound (412 mg, 1.28 mmol, 53% of yield) having chemical structure II ($R_1=R_2=H$) in the form of light yellow oil. The data of $^1$H and $^{13}$C-NMR referring to that is as below.

$^1$H NMR (400 MHz, CDCl$_3$): δ 6.26 (d, J=3.2 Hz, 2H), 6.04 (d, J=3.2 Hz, 2H), 4.48 (q, J=11.7 Hz, 4H), 3.99 (d, J=2.8 Hz, 1H), 3.76 (d, J=3.2 Hz, 1H), 3.73 (d, J=2.8 Hz, 1H), 3.44 (dd, J=11.4, 5.8 Hz, 2H), 3.17-3.14 (m, 2H), 2.79 (t, J=4.6 Hz, 2H), 2.61 (dd, J=4.8, 2.8 Hz, 2H)

$^{13}$C NMR (100 MHz, CDCl$_3$): δ 152.1, 150.5, 77.6, 77.3, 76.9, 65.34, 65.32, 50.4, 44.6.

Preparation Example 3

Preparing a Compound in which $R_1$ is Hydrogen and $R_1$ is a Methyl Group in Chemical Structure II, Using as a Starting Material a Compound in which $R_1$ is Hydrogen and $R_2$ is a Methyl Group in Chemical Structure III (1) Preparing the Compound Having Chemical Structure IV ($R_1=Me, R_2=H$)
[Chemical Reaction Formula 7]

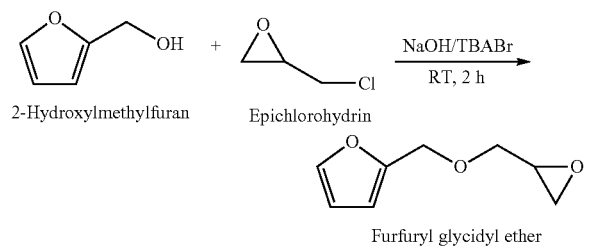

With reference to the chemical reaction formula 7, using 2-furan carboxylic acid methyl ester (1.50 g, 12.0 mmol), acetaldehyde (1.06 g, 24.0 mmol) and H$_2$SO$_4$ (15 mL) of 98%, reaction and work-up are conducted in the same manner as in the preparation example 2. The reaction liquid is then separated by flash chromatography (hexanes:EtOAc=5:1) to obtain a compound (1.78 g, 6.40 mmol, 53% of yield) having chemical structure IV ($R_1=Me, R_2=H$) in the form of light yellow oil. The data of $^1$H and $^{13}$C-NMR referring to that is as below.

$^1$H NMR (400 MHz, CDCl$_3$): δ 7.11 (d, J=3.2 Hz, 2H), 6.22 (d, J=2.8 Hz, 2H), 4.36 (q, J=7.2 Hz, 1H), 3.87 (s, 6H), 1.69 (d, J=7.2 Hz, 3H)

$^{13}$C NMR (130 MHz, CDCl$_3$): δ 159.8, 159.3, 143.8, 119.2, 108.4, 52.0, 33.9, 18.1.

(2) Preparing the Compound Having Chemical Structure III ($R_1=Me, R_2=H$)

Using a compound (1.20 g, 4.54 mmol) having chemical structure IV ($R_1=Me, R_2=H$), LiAlH$_4$ (350 mg, 9 mmol) and anhydrous THF 25 mL, reaction and work-up are conducted in the same manner as in the preparation example 2.

The reaction liquid is then separated by flash chromatography (hexanes:EtOAc=1:1) to obtain a compound (780 mg, 3.51 mmol, 53% of yield) having chemical structure III ($R_1=Me, R_2=H$) in the form of light yellow oil. The data of $^1$H-NMR referring to that is as below.

$^1$H NMR (400 MHz, CDCl$_3$): δ 6.24-6.15 (m, 2H), 6.05-5.90 (m, 4H), 4.60-4.46 (m, 4H), 4.22-4.10 (m, 1H), 1.63-1.54 (m, 3H).

(3) Preparing the Compound Having Chemical Structure II ($R_1=Me, R_2=H$)

Using a compound (300 mg, 1.35 mmol) having chemical structure IV ($R_1=Me, R_2=H$), epichlorohydrin (1.10 mL, 13.5 mmol), NaOH aqueous solution (2.0 g, 250 mmol) of 50% and tetrabutylammonium bromide (0.644 g, 0.20 mmol), reaction and work-up are conducted in the same manner as in the preparation example 2. The reaction liquid is then separated by flash chromatography (hexanes:EtOAc=2:1) to obtain a compound (293 mg, 0.88 mmol, 65% of yield) having chemical structure II ($R_1=Me, R_2=H$) in the form of transparent oil. The data of $^1$H and $^{13}$C-NMR referring to that is as below.

$^1$H NMR (400 MHz, CDCl$_3$): δ 6.32-6.12 (m, 2H), 6.04-5.86 (m, 2H), 4.54-4.32 (m, 4H), 4.24-4.12 (m, 1H), 3.82-3.60 (m, 2H), 3.48-3.32 (m, 2H), 3.20-3.02 (m, 2H), 2.84-2.68 (m, 2H), 2.64-2.48 (m, 2H), 1.59 (d, J=7.2 Hz, 3H)

$^{13}$C NMR (130 MHz, CDCl$_3$): δ 157.1, 150.3, 110.6, 106.7, 70.7, 65.4, 50.9, 44.6, 33.5, 18.2.

Preparation Example 4

Preparing a Compound in which $R_1$ or $R_2$ is a Methyl Group in Chemical Structure II, Using as an Starting Material a Compound in which $R_1$ or $R_2$ is a Methyl Group in Chemical Structure III (1) Preparing the Compound Having Chemical Structure IV ($R_1=Me, R_2=Me$)

[Chemical reaction formula 8]

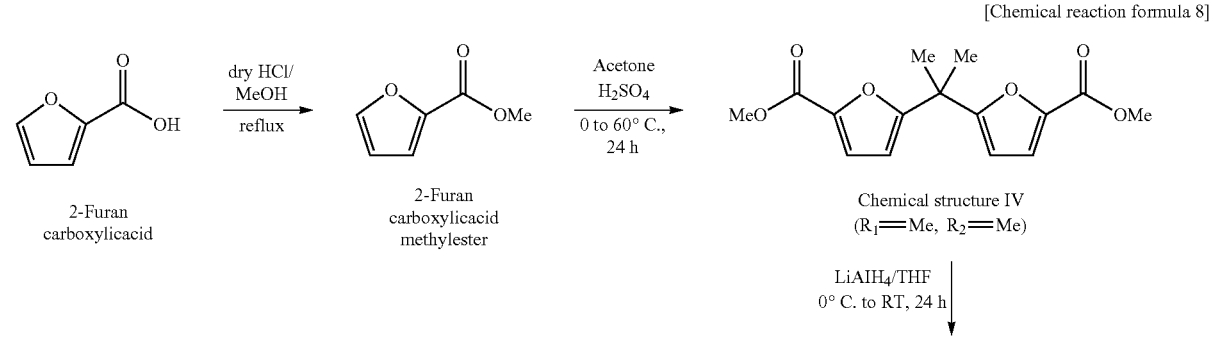

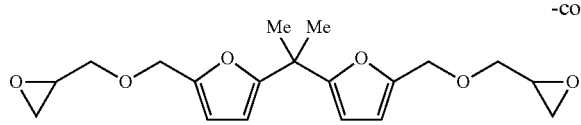

Chemical structure II
($R_1$═Me, $R_2$═Me)

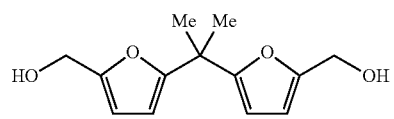

Chemical structure III
($R_1$═Me, $R_2$═Me)

With reference to the chemical reaction formula 8, 2-furan carboxylic acid methyl ester (1.50 g, 12.0 mmol), acetone (1.4 g, 24.0 mmol) and $H_2SO_4$ (15 ml) of 98% are reacted for 24 hours in the same manner as in the preparation example 2, and acetone at the equivalent weight of 1 is added by drops additionally to be further reacted. After reaction work-up under the same condition, the reaction liquid is then separated by flash chromatography (hexanes:EtOAc=5:1) and recrystallized to obtain a compound (1.23 mg, 4.21 mmol, 70% of yield) having chemical structure IV ($R_1$=Me, $R_2$=Me) in the form of light yellow crystallization. The data of $^1$H and $^{13}$C-NMR referring to that is as below.

$^1$H NMR (400 MHz, $CDCl_3$): δ 7.14-7.06 (m, 1H), 6.24-6.16 (m, 1H), 3.86 (s, 3H), 1.74 (s, 3H)

$^{13}$C NMR (130 MHz, $CDCl_3$): δ 163.4, 159.4, 143.7, 119.1, 107.6, 52.0, 38.5, 26.2.

(2) Preparing the Compound Having Chemical Structure III ($R_1$=Me, $R_2$=Me)

Using a compound (1.50 g, 5.20 mmol) having chemical structure IV ($R_1$=Me, $R_2$=Me), $LiAlH_4$ (395 mg, 10.4 mmol), anhydrous THF 50 mL, reaction and work-up are conducted in the same manner as in the preparation example 2. The reaction liquid is then separated by flash chromatography (hexanes:EtOAc=1:1) to obtain a compound (884 mg, 3.74 mmol, 72% of yield) having chemical structure III ($R_1$=Me, $R_2$=Me) in the form of yellow oil. The data of $^1$H-NMR referring to that is as below.

$^1$H NMR (400 MHz, $CDCl_3$): δ 6.18 (d, J=3.2 Hz, 2H), 5.98 (d, J=2.8 Hz, 2H), 4.54 (s, 4H), 1.68-1.60 (m, 8H)

(3) Preparing the Compound Having Chemical Structure II ($R_1$=Me, $R_2$=Me)

Using a compound (1.40 g, 5.92 mmol) having chemical structure IV ($R_1$=Me, $R_2$=H), epichlorohydrin (1.85 mL, 23.7 mmol), NaOH aqueous solution (8.0 g, 100 mmol) of 50% and TBABr (270 mg, 0.84 mmol), reaction and work-up are conducted in the same manner as in the preparation example 2. The reaction liquid is then separated by flash chromatography (hexanes: EtOAc=2:1) to obtain a compound (1.78 g, 5.10 mmol, 86% of yield) having chemical structure II ($R_1$=Me, $R_2$=Me) in the form of transparent oil. The data of $^1$H and $^{13}$C-NMR referring to that is as below.

$^1$H NMR (400 MHz, $CDCl_3$): δ 6.28-6.20 (m, 2H), 6.00-5.92 (m, 2H), 4.52-4.40 (m, 4H), 3.75-3.65 (m, 2H), 3.48-3.38 (m, 2H), 3.18-3.06 (m, 2H), 2.82-2.74 (m, 2H), 2.64-2.56 (m, 2H), 1.63 (s, 6H).

$^{13}$C NMR (130 MHz, $CDCl_3$): δ 160.5, 150.3, 110.4, 105.2, 70.5, 65.4, 50.9, 44.6, 37.7, 26.4.

Comparative Example

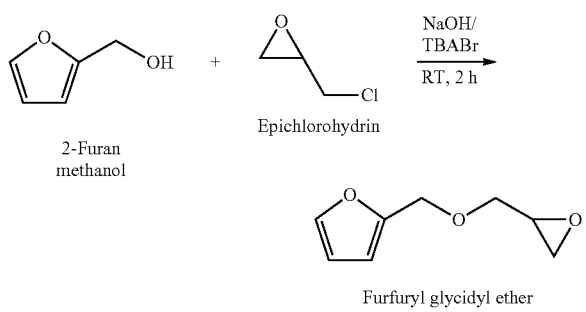

[Chemical reaction formula 9]

2-Furan methanol

Epichlorohydrin

Furfuryl glycidyl ether

With reference to the chemical reaction formula 7, epichlorohydrin (23.5 mL, 300 mmol), NaOH aqueous solution (22.0 g, 275 mmol) of 50% and TBABr (0.644 g, 2 mmol) as a catalyst are put into a 100 mL round-bottom flask one after another, and intensely magnetic stirred. 2-furanmethanol (9.81 g, 100 mmol) diluted in THF 30 mL is then slowly added by drops into the flask at a room temperature, and then intensely stirred for two hours at a room temperature. Afterwards the reaction liquid is moved to a separatory funnel, into which are added distilled water and EtOAc 200 ml each to wash an organic layer twice and washed with saturated NaCl aqueous solution. After moisture in the funnel is removed by $MgSO_4$, the residue having been filtered and vacuum evaporated is separated to flash chromatography (hexanes: EtOAc=1:1→1:2) to obtain a furfuryl glycidyl ether (13.3 g, 86.3 mmol, 86% of yield) in the form of transparent oil. The data of $^1$H and $^{13}$C-NMR referring to that is as below.

$^1$H NMR (400 MHz, $CDCl_3$): δ 7.42-7.40 (m, 1H), 6.35 (s, 2H), 4.58-4.48 (m, 2H), 3.76 (dd, J=11.2, 2.8 Hz, 1H), 3.44 (dd, J=11.2, 5.6 Hz, 1H), 3.20-3.12 (m, 1H), 2.28-2.77 (m, 1H), 2.64-2.59 (m, 1H).

$^{13}$C NMR (100 MHz, $CDCl_3$): δ 151.6, 143.2, 143.1, 110.5, 110.4, 109.9, 109.8, 70.8, 65.2, 50.9, 44.5.

Observing a Curing Behavior (Measuring Photo Curing Time and Curing Contraction Ratio)

Photo curing behavior of the composition containing each compound is studied and the contraction ratio during curing is measured, in order to examine the applicability as a curing material of a furan-based curable compound containing an epoxide functional group which is synthesized as in the preparation example 1 and comparative example.

Measuring a Photo Curing Behavior

Photo-DSC is a device to check photo curing behaviors such as conversion ratio and photo curing rate by inspecting the heat of reaction by installing a photo curing accessory into a conventional DSC and syncing those two. The Photo-DSC is provided by directly connecting Q-1000DSC of TA Instrument Inc. and Photocalorimetric accessory (Novacure 2100). Medium pressure mercury lamp (100 W, Intensity: 50 mW/cm$^2$) is used for light source, and cationic photo curing initiator, IRGACURE 250 is used for curing initiator. Sample containing 1 wt % of photo curing initiator is added into open type aluminum pan 2~3 mg at a time, with light irradiated at 25° C. to measure the amount of the heat of reaction induced from the sample. The result of measuring the photo curing behavior by the Photo-DSC is indicated in FIG. 1 and FIG. 2.

Figure 2:
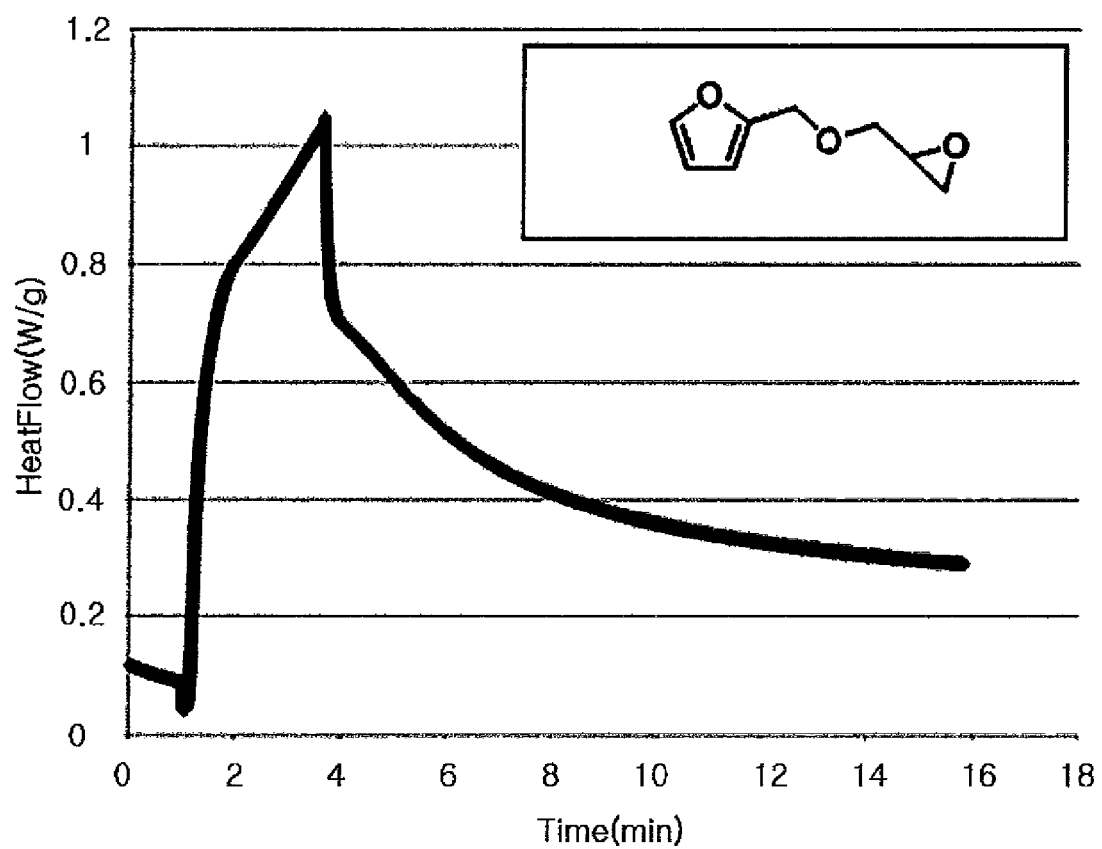
FIG. 2 refers to the result of measuring a photo-curable behavior by Photo-DSC of a curable compound prepared according to comparative example.

Having analyzed the Photo-DSC, as shown in FIG. 1 and FIG. 2, the furan-based curable compound prepared according to the embodiment of FIG. 1 of the invention starts curing after about 1 minute, and it takes more than 10 minutes to cure, which is rather long. However, the furan-based curable compound prepared according to the embodiment of FIG. 1 takes 30% less time to cure than a furan-based curable compound, furfuryl glydicyl ether containing one epoxide functional group prepared according to the comparative example of FIG. 2.

Measuring Photo Curing Contraction Ratio

LVDT (Linear Variable Differential Transformer) transducer and UV Spot curing device are used to measure photo curing contraction ratio. This method is to evaluate the curing contraction ratio which is obtained during photo curing using the UV-Spot curing device, based on the principle of measuring the linear variations using unattached LVDT. RB308 Linometer™ of R&B Inc.'s Linometer System is used for the contraction ratio measuring device, and SP-7 of Ushio Inc. is used for the UV-Spot curing device. After a stainless disk is arranged at regular intervals on the unattached linear displacement sensor, which can measure length by using magnetic field, certain thickness or certain amount of sample is loaded on the disk. A slide glass is spread out over resin and is fixed to the resin. Light source is fixed at a certain height of the slide glass. Afterwards the sensor is operated with UV being irradiated at the same time, allowing the stainless disk to be lifted upwards to the slide glass, and broadening the interval between the sensor and the stainless disk. The interval is recorded to measure the degree of contraction, and the result is shown in the following table 1.

tion ratio. Therefore, the furan-based curable compound derived from biomass according to the invention is considered appropriate to be used in the fields where precise measuring is required such as in the field of electronic materials.

Measuring Adhesive Strength

Adhesive strength is the most basic property to show a functionality as adhesives, and in this experiment lap shear strength is measured using UTM device. H100KS of HOUNSFIELD Inc. is used to measure the properties, and QMat (ver. 5.37) software is used to calculate the measurement. Transparent polycarbonate is used for an object to which adhesives are attached, with light transmittancy taken into consideration. For a test specimen, two objects to which adhesives are attached, with the fixed size (1 inch×4 inch×0.2 inch=width×length×thickness) based on ASTM D 5868-01 standard, are overlapped 1 inch×1 inch, and in between the overlapped surfaces are spread with adhesive materials. When fixing each test specimen to the UTM, each end grip of the test specimen is set at 1 inch, and the test specimen is pulled at the speed of 0.5 inch/min to measure the shear strength. Fixed amount of 20 μL of the adhesive materials is spread out, and it is cured by irradiating UV at the strength of 200 mW/cm$^2$ for a certain time.

Figure 3:
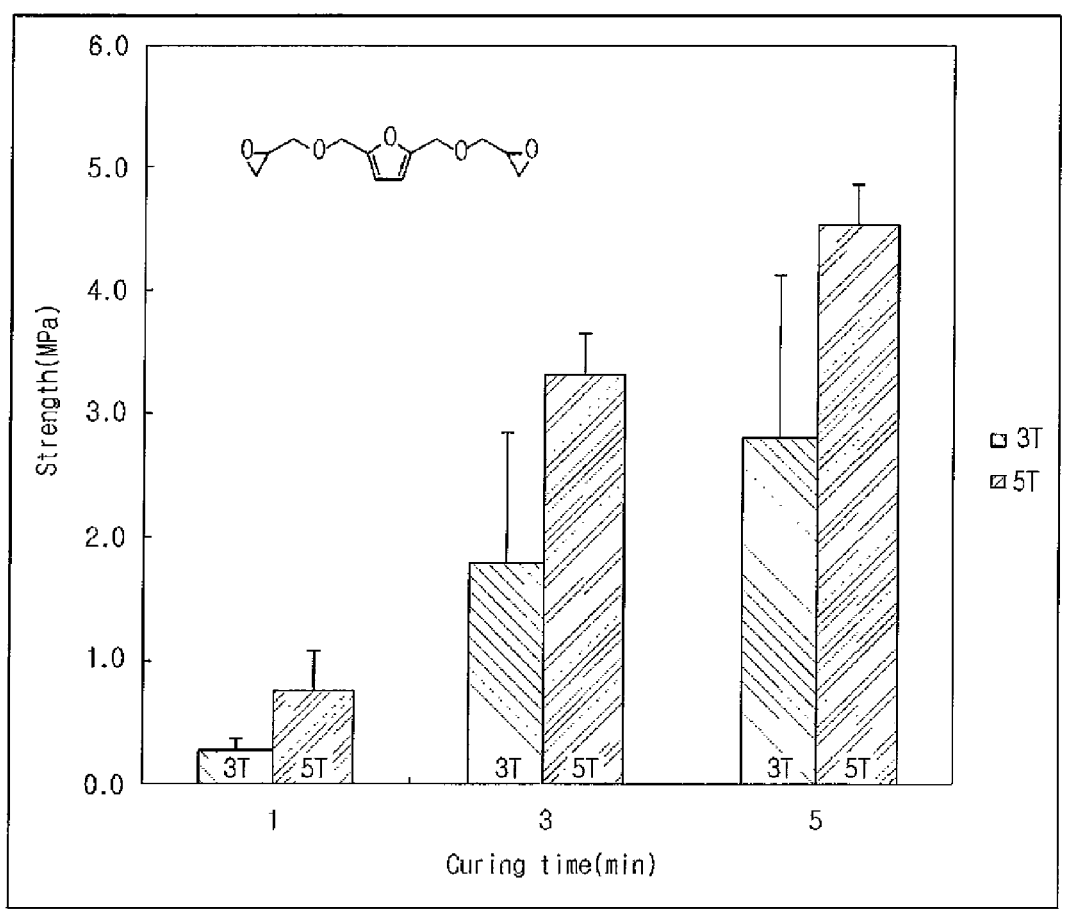
FIG. 3 refers to the result of measuring adhesive strength of a curable compound prepared by preparation example 1 of the invention. (X axis: UV irradiation time, Y axis: adhesive strength)
Figure 4:
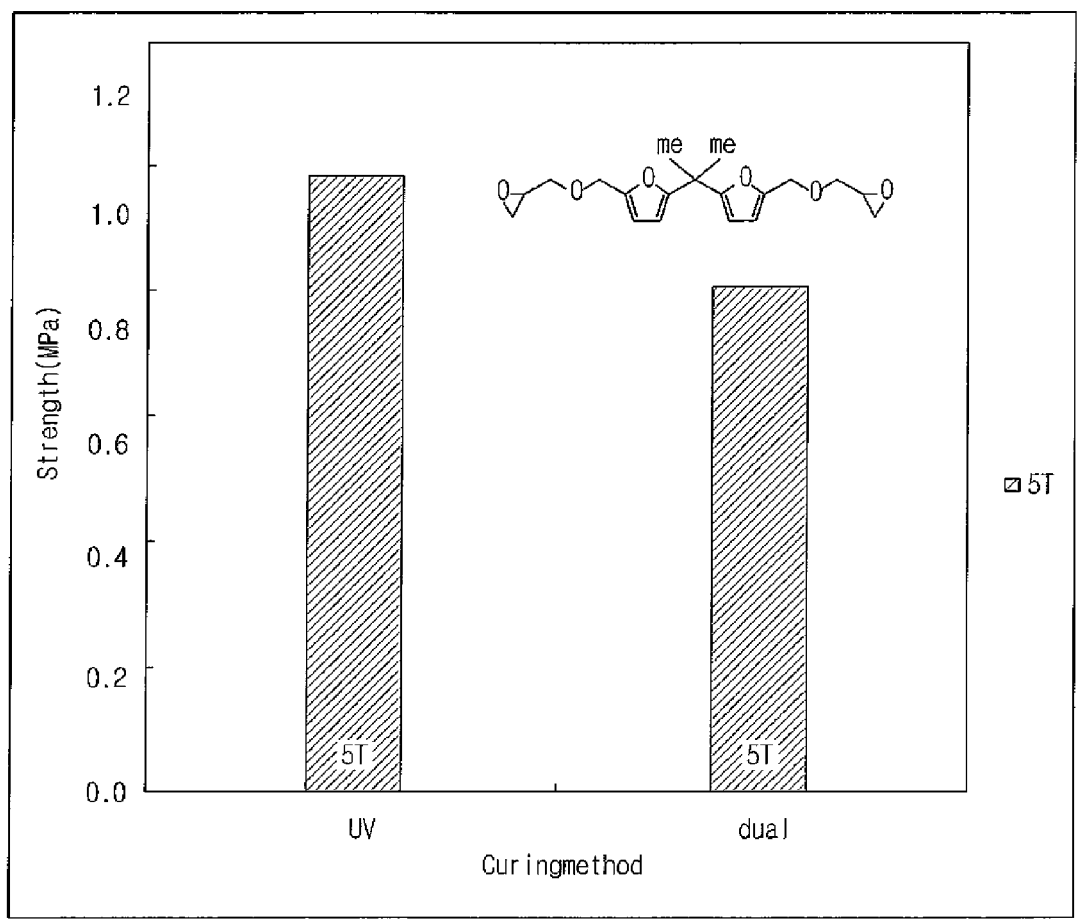
FIG. 4 refers to the result of measuring adhesive strength of a curable compound prepared by preparation example 4 of the invention. (X axis: curing method, Y axis: adhesive strength)

As for the result of measuring the adhesive strength, as shown in FIG. 3 and FIG. 4, if the compound having chemical structure I is cured by putting in an initiator of 5 wt % and irradiating UV for 5 minutes, the adhesive strength reaches up to 4 MPa, while the compound having chemical structure II ($R_1$=Me, $R_2$=Me) manifests the adhesive strength of about 1 MPa. It is deemed that the compound having chemical structure I which is relatively low in hydrophobicity as well as steric hindrance effect has more compatibility with the polycarbonate to which adhesives are attached than the compound having chemical structure II ($R_1$=Me, $R_2$=Me). It is regarded that self-cohesion is more likely to occur more than adhesion during curing of the compound having chemical structure II ($R_1$=Me, $R_2$=Me). On the other hand, dual curing, in which additional curing is conducted after photo curing, does not have much influence over the adhesive strength, supposedly the reason being the curing has almost been completed under the light source curing conditions above.

TABLE 1

| | Chemical structure of central compound | Curing contraction ratio(%) |
|---|---|---|
| Preparation example 1 | [structure] | 4.9% |
| Comparative example | [structure] | Unmeasurable |

The furan-based curable compound derived from biomass according to the preparation example 1 of the invention shows excellent efficiency in that it has 4.9% of curing contraction ratio as indicated in the table 1, compared to acryl-based photo-curable materials generally showing about 10% of the curing contraction ratio.

On the other hand, the furan-based compound prepared according to the comparative example is low in viscosity and fast in wetting, making it impossible to measure the contrac- Detailed descriptions are provided above primarily within the preparation examples and comparative example of the present invention.

However, the preparation examples and comparative example given above should not be construed as limiting. Therefore, the invention is not limited merely to the examples described above, but is inclusive of those easily changeable or deletable within the scope of the present invention. Other modifications, variations of the invention may be practiced by those of ordinary skill in the art, without departing from the spirit and scope of the present invention.

What is claimed is:

1. A furan-based curable compound derived from biomass comprising two epoxide functional groups bonded to at least one furan-based compound, wherein the compound has chemical structure I,

[Chemical structure I]

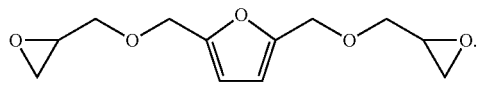

2. A solvent-free curable composition comprising the compound according to claim 1 and an initiator.

3. The solvent-free curable composition according to claim 2, wherein the initiator is a cationic curing initiator.

* * * * *